(12) United States Patent
Fajt et al.

(10) Patent No.: US 9,732,372 B2
(45) Date of Patent: Aug. 15, 2017

(54) USE OF RAPID ONSITE BACTERIA TEST FOR OIL AND GAS APPLICATIONS

(71) Applicant: M-I L.L.C., Houston, TX (US)

(72) Inventors: James R. Fajt, College Station, TX (US); Natasha Shakib, Katy, TX (US)

(73) Assignee: M-I L.L.C., Houston, TX (US)

( * ) Notice: Subject to any disclaimer, the term of this patent is extended or adjusted under 35 U.S.C. 154(b) by 0 days.

(21) Appl. No.: 14/648,428

(22) PCT Filed: Nov. 25, 2013

(86) PCT No.: PCT/US2013/071702
§ 371 (c)(1),
(2) Date: May 29, 2015

(87) PCT Pub. No.: WO2014/085333
PCT Pub. Date: Jun. 5, 2014

(65) Prior Publication Data
US 2015/0337357 A1 Nov. 26, 2015

Related U.S. Application Data

(60) Provisional application No. 61/731,347, filed on Nov. 29, 2012.

(51) Int. Cl.
| | | |
|---|---|---|
| *A61L 2/08* | (2006.01) | |
| *A61L 2/10* | (2006.01) | |
| *C12Q 1/64* | (2006.01) | |
| *C02F 1/00* | (2006.01) | |
| *C02F 1/02* | (2006.01) | |
| *C02F 1/30* | (2006.01) | |
| *C02F 1/32* | (2006.01) | |
| *C02F 1/44* | (2006.01) | |
| *C02F 103/10* | (2006.01) | |

(52) U.S. Cl.
CPC ........... *C12Q 1/64* (2013.01); *A61L 2/087* (2013.01); *A61L 2/10* (2013.01); *C02F 1/008* (2013.01); *C02F 1/02* (2013.01); *C02F 1/30* (2013.01); *C02F 1/32* (2013.01); *C02F 1/444* (2013.01); *C02F 2103/10* (2013.01); *C02F 2303/04* (2013.01)

(58) Field of Classification Search
CPC .................. A61L 2/087; A61L 2/10
See application file for complete search history.

(56) References Cited

U.S. PATENT DOCUMENTS

| | | | |
|---|---|---|---|
| 4,503,149 A | 3/1985 | Boyd | |
| 5,093,236 A | 3/1992 | Gonzales-Prevatt et al. | |
| 7,939,285 B2 * | 5/2011 | Reeslev | C12Q 1/04 435/29 |
| 2007/0129259 A1 * | 6/2007 | Abney | C02F 1/32 507/200 |
| 2007/0178446 A1 * | 8/2007 | Reeslev | C12Q 1/04 435/5 |
| 2008/0115945 A1 | 5/2008 | Lau et al. | |
| 2010/0248997 A1 | 9/2010 | Li et al. | |
| 2011/0284219 A1 * | 11/2011 | Pomerantz | E21B 49/10 166/264 |
| 2012/0115723 A1 | 5/2012 | Stimson et al. | |
| 2012/0181028 A1 | 7/2012 | Daussin et al. | |
| 2012/0261117 A1 | 10/2012 | Pavia et al. | |
| 2012/0283148 A1 * | 11/2012 | Dobson, Jr. | C09K 8/04 507/103 |

FOREIGN PATENT DOCUMENTS

| | | |
|---|---|---|
| CA | 2750872 A1 | 8/2010 |
| FR | 2880035 A1 | 6/2006 |
| WO | 2012-094007 A2 | 7/2012 |
| WO | WO 2012-000940 * | 7/2012 |

OTHER PUBLICATIONS

Bass et al 1997 (Oilfield Rev 9:17-25).*
Bass, et al., "The Bad Guys and the Good Guys in Petroleum Microbiology," Oilfield Rev, 1997, vol. 9, pp. 17-25.
International Search Report and Written Opinion issued in International Application No. PCT/US2013/071702; Dated Mar. 10, 2014 (10 pages).
Extended European Search Report issued in European Application No. 13859278.7; Dated May 10, 2016 (7 pages).
Examiner's Requisition (Office Action) dated Aug. 2, 2016, issued by the Canadian Intellectual Property Office in related Canadian Patent Application No. CA 2,892,963 (4 pages).
Petruzzi, Nicholas M., et al., "A Sampling Device for Collection of Ground Water Bacteria under Natural Gradient Flow Conditions"; Ground Water Monitoring and Remediation, vol. 26, No. 1, Feb. 2006; DOI: 10.1111/i.1745-6592.2006.00061.x; pp. 85-91 (10 pages) (downloaded from Google, https://www.researchgate.net/publication/227664661, Feb. 10, 2017.) [Claims 1-8, 11-14, and 16-19].
Brock, et al., "Biology of Microorganisms," Prentice-Hall, Inc., Englewood Cliffs, N.J., USA, 9th edition, 2000.
Richard P. Haugland, "Molecular Probes: Handbook of fluorescent probes and research products," 9th edition, 2002, Chap 10, pp. 397-448.
D.B. Bennion, et al., "Mechanisms of Formation Damage and Permeability Impairment Associated With the Drilling, Completion and Production of Law API Gravity Oil Reservoirs," SPE 30320, MS SPE Conference Paper, 1995.
Boschee, "Handling Produced Water from Hydraulic Fracturing"; Oil and Gas Facilities; pp. 22-26; Feb. 2012.
Communication pursuant to Rule 114(2) EPC for the equivalent EP patent application 13859278.7 dated Oct. 19, 2015.
Communication pursuant to Rule 114(2) EPC for the equivalent EP patent application 13859278.7 dated Nov. 11, 2015.

* cited by examiner

*Primary Examiner* — Padma V Baskar
(74) *Attorney, Agent, or Firm* — Sara Hinkley

(57) ABSTRACT

A method for onsite bacteria testing for oil and gas applications including collecting at least one component of a wellbore fluid; exposing at least one contaminant in the at least one component to at least one substrate that produces a detectable moiety; and performing a quantitative or qualitative detection of the detectable moiety.

5 Claims, No Drawings

USE OF RAPID ONSITE BACTERIA TEST FOR OIL AND GAS APPLICATIONS

BACKGROUND

Many oilfield operations occur with a fluid be circulated through or otherwise introduced into the borehole. These fluids may include drilling fluids that are circulated during the drilling of the well, completion fluids that may be circulated during or after drilling during various completion operations, and fracturing fluids which may be used after drilling in order to stimulate the well to increase production from a hydrocarbon reservoir.

After a well is drilled into a subterranean geological formation that contains oil, natural gas, and water, efforts are made to maximize the production of the oil and/or gas. To increase the permeability and flow of the oil and/or gas to the surface, the drilled wells are often subjected to well stimulation. Well stimulation generally refers to several post drilling processes used to clean the well bore, enlarge channels, and increase pore space in the interval to be injected thus making it possible for fluids to move more readily into the formation.

A well stimulation process may generally include pumping engineered fluids at high pressure and rate into the subterranean geological formation. The fluid (usually water with some specialty high viscosity fluid additives) exceeds the rock strength and opens a fracture in the formation, which can extend out into the geological formation for as much as several hundred feet. Certain commonly used fracturing treatments generally comprise a carrier fluid (usually water or brine) and a polymer, which is also commonly referred to as a friction reducer. Many well stimulation fluids will further comprise a proppant. Other compositions used as fracturing fluids include water with additives, viscoelastic surfactant gels, gelled oils, crosslinkers, oxygen scavengers, and the like.

Water may be used in all of these processes as a component of wellbore fluids, as well as in other types of fluids not specifically mentioned. However, the water used in wellbore fluids may contain microbes, such as bacteria, fungus, etc., that can grow and proliferate on the surface or downhole. Biocides and antimicrobials may be used to control microbial growth in the water. As used herein, "control" is defined to include both inhibition and removal. If left untreated, microbes and microbial biofilms (slimes) can cause deterioration of equipment, loss off efficiency in equipment, promotion and acceleration of corrosion on metal surfaces, or increased down time.

SUMMARY

In one aspect, embodiments disclosed herein relate to a method including collecting at least one component of a wellbore fluid; exposing at least one contaminant in the at least one component to at least one substrate that produces a detectable moiety; and performing a quantitative or qualitative detection of the detectable moiety.

In another aspect, embodiments disclosed herein relate to a method including determining a concentration of a microbial population in a wellbore fluid; treating the wellbore fluid to reduce the microbial population and produce a treated wellbore fluid; and determining a concentration of the microbial population in the treated wellbore fluid.

This summary is provided to introduce a selection of concepts that are further described below in the detailed description. This summary is not intended to identify key or essential features of the claimed subject matter, nor is it intended to be used as an aid in limiting the scope of the claimed subject matter. Other aspects and advantages of the disclosure will be apparent from the following description and the appended claims.

DETAILED DESCRIPTION

In one aspect, embodiments disclosed herein are generally directed to on-site testing for bacteria content of oilfield water based solutions and more particularly, adjusting or treating oilfield water based solutions based on the on-site testing results.

In another aspect, embodiments disclosed herein are generally directed to a method for treating oilfield water based solutions based on the on-site testing results. The method includes determining the concentration of a microbial population in the wellbore fluid; treating the wellbore fluid with to reduce the microbial population and produce a treated wellbore fluid; determining the concentration of the microbial population in the treated wellbore fluid. The treated wellbore fluid may be repeatedly treated to further reduce the microbial population and produce a final wellbore fluid having an acceptable level of contaminants.

The concentration of a microbial population may be determined by on-site test methods. After the concentration of the microbial population is determined, the wellbore fluid may be subjected to at least one treatment process to produce a treated wellbore fluid. The at least one treatment process may be selected from the group consisting of chemicals; ultra violet radiation (UV); ultra-filtration; thermal; ionizing radiation; and non-ionizing radiation or any other treatment process known to one of ordinary skill in the art for reducing the concentration of a microbial population.

In some embodiments, the chemicals may include biocides or oxygen scavengers for controlling bacterial growth and oxygen degradation, respectively. In some embodiments, the biocide is selected to have minimal or no interaction with any of the components in the wellbore fluid. In other embodiments, the biocide is selected to have interaction with the components in the wellbore fluid, for example the components may include chemicals and sand. For example, the biocide should not affect fluid viscosity to any significant extent and should not affect the performance of oxygen scavengers contained within the fluid.

Other desirable properties for the biocide include (a) cost effectiveness, e.g., cost per liter, cost per square meter treated, and cost per year; (b) safety, e.g., personnel risk assessment (for instance, toxic gases or physical contact), neutralization requirements, registration, discharge to environment, and persistence; (c) compatibility with system fluids, e.g., solubility, partition coefficient, pH, presence of hydrogen sulfide, temperature, hardness, presence of metal ions or sulfates, level of total dissolved solids; (d) compatibility with other treatment chemicals, e.g., corrosion inhibitors, scale inhibitors, demulsifiers, water clarifiers, well stimulation chemicals, and polymers; and (e) handling, e.g., corrosiveness to metals and elastomers, freeze point, thermal stability, and separation of components.

In some embodiments, wellbore fluids may employ either glutaraldehyde or tetra-kis-hydroxymethyly-phosphonium sulfate (THPS) to control bacterial contamination. In other embodiments, one skilled in the art may determine the type of biocide and/or oxygen scavenger to treat the wellbore fluid based upon the type and amount of the microbial population in the wellbore fluid. Other examples of fluids which can be used to control microbial populations include quaternary ammonia, sodium hypochlorite, chlorine dioxide, hydrogen peroxide, ozone, bromous acid, and perchloric acid.

After an initial treatment has been done to the wellbore fluid, the concentration of the microbial population in the treated wellbore fluid may be determined by on-site test methods. After the concentration of the microbial population is determined, subsequent treatment and testing may be repeated until the microbial population is at an acceptable level. The term "acceptable" refers to any amount of contaminants that one of ordinary skill in the art would deem as not being detrimental to the oilfield operations. The subsequent treatment may be the same as the initial treatment or may be changed depending on the efficacy of the initial treatment fluid.

In some embodiments, the treatment is selected to have minimal or no interaction with any of the components in the wellbore fluid. In other embodiments, the treatment may be selected to interact with the components in the wellbore fluid. Components of the wellbore fluid may include solids and liquids such as, for example, raw water, chemicals and sand. For example, the treatment should not affect fluid viscosity to any significant extent and should not affect the performance of oxygen scavengers contained within the wellbore fluid.

In another aspect, embodiments disclosed herein are generally directed to a method for preparing a wellbore fluid. Examples of the wellbore fluid may include raw water, chemicals, and sand, or combinations thereof. The method may include determining the concentration of the microbial population in a raw water stream by the on-site test methods; and treating the raw water stream to reduce the microbial population. Treatment may include chemicals and processes (described above) to reduce microbial populations. Chemicals and sand may be added to the treated raw water to produce a wellbore fluid. In some embodiments, the chemicals and/or sand may provide an amount of a microbial population and/or interact with the microbial population in the raw water to produce an amount of the microbial population greater than originally determined for the raw water alone. Therefore, after the raw water interacts with the chemicals and/or sand, the concentration of the microbial population in the wellbore fluid may be determined by the methods described above and the wellbore fluid may be treated (as described above) to produce a final wellbore fluid having an acceptable level of a microbial population. Examples of wellbore fluids include, but are not limited to, drilling fluids, completion fluids and fracturing fluids.

A portable system, method and apparatus are therefore needed for effectively and economically treating source water and produced water to an acceptable level of a microbial population, specifically bacteria. Other beneficial advantages achievable through use of embodiments disclosed herein include, for example, the capability for reliably controlling the chemistry and additive levels in treated water; for independently recirculating, treating and adjusting the chemistry of and additive levels in fluids maintained in individual frac tanks; and, if a leak or overflow of a frac tank occurs, minimizing the amount of treating chemical that is released to the environment with far less harmful environmental impact than would likely be experienced if using traditional water treatment chemistries and methods. In some embodiments, the method of determining the microbial population of a wellbore fluid is performed on-site at a location wherein the wellbore fluid is being used.

Biocides are often used in the oil or gas field for remediation or prevention purposes. For example, biocides are often applied to reduce or "knockdown" the high numbers of microbial populations in formulations that are pumped downhole in connection with drilling, completion, fracturing ("fracking"), reinjection or other oil or gas field operations. The microbial populations may be found in raw water sources in wellbore fluids, but may also be present in other additive sources such as in chemicals and/or sand. The raw water may contain microbial populations including microbes, such as but not limited to bacteria, fungi, algae, protozoans, spores from bacteria, fungal spores, and pollen, and fragments thereof, which may interfere with the efficacy of the wellbore fluids or the equipment used in oilfield operations.

While biocide compositions are available that provide adequate biocidal activity in downhole operations, the testing of the oilfield fluids will conventionally take weeks to provide information regarding the efficacy of the biocide. The efficacy of the biocide (or any treatment process) may be affected by the biocide composition, the dosing amount of the biocide, and outside factors such as, but not limited to, chemical and/or sand compositions used in the wellbore composition.

An on-site way of providing results of microbial population activity testing in the wellbore fluid may provide operators with information for adjusting the biocide composition (or treatment process) or the amount without the delay of shipping sample volumes offsite and would also reflect real time microbial content as compared to a delayed microbial content. With the knowledge of the microbial population activity, formulation of the wellbore fluid can be adjusted and monitored to provide a type of treatment to minimize fouling in the wellbore operations. It would be also be helpful to determine if the treatment is compatible with other components used in downhole operations, is relatively non-corrosive to metals, is capable of providing rapid microbiocidal activity promptly upon reaching the downhole regions, and is effective against a variety of aerobic and anaerobic bacterial species including sulfate-reducing species that produce hydrogen sulfide and resultant "souring" of the hole.

Tests for detecting microbial populations in water based wellbore fluid suspected of containing such microbial populations may include collecting at least one component of the wellbore fluid. In some embodiments, the at least one component may be a liquid or a solid. If the at least one component is a solid, it may be mixed with a liquid. The liquid may be selected from group consisting of water, surfactants, emulsifiers, biocides, corrosion inhibitors, friction reducers, crosslinkers, or formulated fracturing fluids. The at least one component of the wellbore fluid may be obtained from any known sampling device. The at least one component may be collected prior to the wellbore fluid entering the wellbore or after the wellbore fluid has been downhole and re-circulated to the surface. Once collected, the at least one component of the wellbore fluid may be tested. In some embodiments, the at least one component may be collected after the wellbore fluid has been treated to reduce contaminants.

Methods disclosed herein can be applied to samples from various sources, the rule being that it should be possible to integrate the contaminant-containing sample into a medium, the properties of which allows that it can be passed through a filter. In some embodiments, the medium is a liquid medium, such as but not limited to, for example, water. In some embodiments, the at least one component may be a sample of extractable solids can be obtained from environmental samples such as soil, sediments, plants, clothing (e.g.

sterile garments), furs and feathers etc. Contaminants from such environmental samples are extracted using an extraction liquid and the extraction liquid is subsequently subjected to methods disclosed herein.

The test to determine the concentration of bacteria is by any known testing process known to one skilled in the art which provides microbial population concentration. One example of a test for measuring microbial population concentration includes that described in U.S. Pat. No. 7,939,285, herein incorporated by reference in its entirety; however, no limitation exists on the type of microbial population test to be used in conjunction with embodiments of the present disclosure.

In some embodiments, the testing may include the following steps: a) collecting at least one component of a wellbore fluid; b) exposing at least one contaminant in the at least one component to at least one substrate that produces a detectable moiety In other embodiments, the testing may include the following steps: a) passing a known volume of said medium through a filter from an influent side to an effluent side in a filter device thereby concentrating the contaminants on the influent side of the filter in the filter device; b) contacting the influent side of the filter in the filter device with a liquid vehicle containing at least one substrate, wherein said at least one substrate through interaction with an enzyme characteristic of the contaminants produces a detectable moiety; c) allowing the substrate to interact with the contaminants on the influent side of the filter in the filter device for a period of time, which is sufficient to allow the detectable moiety to be detected in the liquid vehicle; d) evacuating the liquid vehicle from the influent side of the filter by forcing the liquid vehicle through to the effluent side of the filter; and e) performing a quantitative or qualitative detection of the detectable moiety in the liquid vehicle evacuated in step d and correlating the detection of the moiety to the amount or presence of contaminants in the sample.

In some embodiments, it will be relatively simple to ensure that the amount of detectable moiety which is produced can be translated into a "contaminant number". It may suffice to provide a qualitative result (of the type "contamination" or "no contamination") because it is merely of interest to determine whether or not a certain threshold value has been exceeded. In other embodiments, knowledge of the sample type and the system from where it is derived will ensure that one single pass of the method provides for a precise determination of the contamination count—it is simply a question of ensuring a surplus of substrate in step b so that the enzyme is saturated.

The period of time referred to in step c is the time interval which allows formation of sufficient amounts of the detectable moiety so as to render detection thereof possible. In some embodiments, this time interval is conveniently less than 24 hours, but normally much shorter, such as, at the most 12, 11, 10, 9, 8, 7, 6, 5, 4, 3, 2, and 1 hours. In other embodiments, normally the time interval will not be less than 5 minutes and it is in most cases not less than 20 minutes.

In some embodiments, it may be desirable to subject the wellbore fluid to a pre-filtration step to screen out large-size material that might interfere with a subsequent detection or to concentrate the at least one contaminant in the at least one component to produce a concentrated sample. Such a pre-filter should have a pore size, which allows passage of the contaminants but which does not allow passage of larger-sized materials such as irrelevant solid particles. In some embodiments, this two-step filtration can be combined with application of steps b and c of the method on both the pre-filter and of the filter where the prefiltered sample has been passed through (the primary filter). By doing this, it becomes possible to add the two measurements in order to obtain a measure for the total contamination.

The term "filter" includes devices that exclude passage of particles larger than a certain size. However, the term can also embrace a device that excludes passage of material that has a binding specificity towards a binding partner (such as a receptor, an antibody or fragments thereof). Therefore, the term also embraces devices not normally regarded as "filters", e.g. membranes in centrifuges and ultracentrifuges, membranes impregnated with specific binding partners such as antibodies or other specifically binding substances. Specialized "filters" may include columns for affinity chromatography. Features of a "filter" according to embodiments disclosed herein include it can retain contaminants of interest and allow a subsequent in situ reaction between a substrate and an enzyme specific for the contaminants so that a subsequent measurement of a detectable moiety derived from the substrate can be readily performed.

The filter may have a pore size small enough so as to retain substantially all contaminants in the wellbore fluid. That is, all contaminants of interest. In some embodiments, it may be of interest to prepare the sample to allow detection of certain contaminants (e.g. not the above-mentioned fragments of bacteria, fungi or spores) the pores can be set to a size that will allow such contaminants to pass through the filter. However, since there are large differences between e.g. protozoan cells and certain bacteria, the pore size of the filter can vary. Also, in order to "catch" contaminants having defined sizes, the method may be run in several parallel tracks, each using its own pore size in step a; for example, simple subtraction of two measurements obtained from different pore sizes will provide information of the presence of contaminants having a size in the interval between the two pore sizes.

Consequently, in some embodiments, the pore size is at most about 20 µm, in other embodiments at most about 15, at most about 10, at most about 5, and at most about 3 µm. For retaining spores or fragments of microorganisms, even smaller pore sizes may be utilized.

Further, in many embodiments, the pore size should be large enough to let the detectable moiety pass through the filter; this is of essence when a subsequent detection is performed on the liquid medium which has been evacuated by forcing it through and away from the filter. In this context, the pore size is at least about 0.1 µm (but may be larger such as at least about 0.22 µm or at least about 0.45 µm), but again, the suitable pore size depends on the choice of detectable moiety.

The term "signal" is intended to denote the measurable characteristic of a detectable moiety as it is registered in an appropriate measuring system.

The term "substrate" means a chemical agent that undergoes an enzyme-catalyzed conversion in its chemical structure. The at least one substrate used, according to embodiments disclosed herein, may conveniently produce a detectable moiety by being cleaved (or otherwise chemically converted) by an enzyme that is characteristic for the contaminants. By this is meant that the enzyme in question is biochemically active in the contaminants which are the objective to determine The term "detectable moiety" may denote a chemical entity which is the result of an enzyme-catalyzed conversion of a substrate, where the chemical entity comprises a physical or chemical characteristic which can be detected and which is not detectable in the substrate.

Examples are fluorescent moieties, luminescent moieties, and moieties that bind with high specificity to a binding partner. In some embodiments, both detection of total contamination and detection of contamination with certain subsets or species of contaminants are capable. In the first case, it may be convenient to use a substrate that is converted by a phylogenetically preserved enzyme, i.e., an enzyme or enzyme activity that exists in highly homologous form in practically all contaminants of biological origin, i.e., in most living or viable microorganisms. In the latter case, it may be convenient to use a substrate that is converted by an enzyme that is highly specific for the relevant contaminants. At any rate, the enzyme may be selected from the group consisting of carbohydrases, proteases, lipases, esterases, amidases, sulfatases, nucleases, and phosphatases such as alkaline phosphatase.

In some embodiments, it is also possible to use at least two substrates that produce detectable moieties providing distinguishable signals. Several different groups of contaminants can be determined individually.

In some embodiments, the enzyme that processes the substrate is expressed constitutively by microorganisms. This has the advantage that induction of enzyme production in the contaminants should be unnecessary—it is further relevant to point out that induction of enzyme activity could be a source of error and uncertainty because control over the induction might be difficult to achieve.

Hence, enzymes which may be used in the present method include those naturally produced in a microbial/bacterial cell and in accordance with embodiments disclose herein. For example, detectable enzymatic activities may be activities that are expressed constitutively, expressed in all growth phases of the microbial target population/bacteria and/or expressed independently of the physiological state of the microbial target population/bacteria. The enzymatic activity may be intracellular and/or extracellular. The method may include the detection and quantification of an enzymatic activity selected from enzymes hydrolyzing substrates providing essential nutritional elements for the growth of the target microbial population/bacteria. The expression "essential nutritional elements" indicate nutrients as defined in e.g. Brock et al., Biology of Microorganisms, Prentice-Hall, Inc., Englewood Cliffs, N.J., USA. Thus, essential nutritional elements include nutrients, without which a cell cannot grow and include macronutrients as well as micronutrients. Accordingly, the present method can be based upon detection of a microbial/bacterial enzyme involved in carbohydrate, protein, phosphate and/or sulfate metabolism. In some embodiments, the present method is based upon the detection of microbial phosphatase enzymes. In other embodiments, the method may be based upon detection of alkaline phosphatase involved in phosphate metabolism including the hydrolysis of phosphate esters, including esters of primary and secondary alcohols, sugar alcohols, cyclic alcohols, phenols and amines, liberating inorganic phosphate. The enzyme also hydrolysis polyphosphates $PP_1$ and the transfer of a $PO_4^{3-}$-group from $PP_1$ (and from a number of nucleoside di- and triphosphates and from mannose-6-phosphate) to glucose, forming glucose-6-phosphate. The alkaline phosphatase activity measurements may provide a robust measurement of microbial numbers.

In some embodiments, substrates may be fluorogenic or chromogenic substrates producing blue, green and red products (fluorescent or luminescent etc.) as the detectable moiety. Detection of light emission is a highly convenient and fast way of obtaining information of the presence of relevant moieties. Useful substrates in this context are disclosed in Molecular Probes: Handbook of fluorescent probes and research products, ninth edition, author: Richard P. Haugland, chapter 10, pages 397-448.

Examples of substrates, which are suitable for the methods described, may be selected from the group consisting of 5-bromo-4-chloro-3-indolyl phosphate disodium salt; 9h-(1,3-dichloro-9,9-dimethylacridine-2-one-7-yl) phosphate ammonium salt; fluorescein diphosphate tetraamonium salt; a methylumbelliferyl derivative such as 6,8-difluoro-4-methylumbelliferyl phosphate, 4methylumbelliferyl phosphate dicyclohexylammonium salt trihydrate, 4-methylumbelliferyl phosphate free acid; 4-methylumbelliferyl phosphate dilithium salt, 4-methylumbelliferyl-.beta.-N-acetylglucosaminide, and trifluoromethylumbelliferyl phosphate; salts of 4-nitrophenyl phosphate; and resorufin phosphate.

Regardless of the substrate chosen, in various embodiments, the detectable moiety should be detectable in amounts of at the most 100 picomoles, at the most 50 picomoles, at the most 20 picomoles, at the most 10 picomoles, or at the most 1 picomole. The lower the detection limit is for a particular selectable moiety, the higher is the sensitivity of embodiments of the methods described.

In some embodiments, performing a quantitative or qualitative detection of the detectable moiety in the liquid vehicle evacuated in step d and correlating the detection of the moiety to the amount or presence of contaminants in the sample may be performed by a number of conventional ways generally known to the person skilled in the art.

Besides being based on the detection of a microbial/bacterial enzymatic activity correlated with the quantity of e.g., the viable microbial target population/bacteria, the present method includes any other assay procedure permitting the detection of enzymes which are correlated with the quantity of the contaminants. Such procedures include as examples detecting the amount of microbial/bacterial enzyme immunologically and the detection of DNA and/or RNA sequences coding for the enzymatic activity of interest. Such procedures can be based on methods well-known in the art and include e.g., the use of antibodies, optionally labeled with detectable moieties and the use of oligonucleotide probes that hybridize selectively to the DNA or RNA sequences.

The determination may be immunological or by any other suitable method that detects interaction between the detectable moiety and a specific binding partner (that is: receptor interactions, antibody or antibody fragment interactions, quenching or enhancement reactions where the detectable moiety quenches or enhances a standard signal through some kind of interaction, etc). In some embodiments, step d is performed by measuring fluorescence characteristic of the detectable moiety. This is a rapid, reliable and easy-to-use method that does not require any particular skills from the person who handles the measurement.

As mentioned above, the fluorescence in step d can be measured directly on the liquid vehicle without an interruption of the contact between the liquid vehicle and the contaminants Typically, this will be done when the conversion of the substrate is surveyed continuously or several times so that a relationship over time and amount of detectable moiety can be established--if this relationship is linear, given the fluorescence value for a given time point can be easily correlated to a standard curve over fluorescence vs. contaminant number.

Measurement of fluorescence is a technique well-known in the art, and requires excitation of a fluorophore with electromagnetic waves (typically ultraviolet or visual light)

having a shorter wavelength than the fluorescent emission from the excited fluorophore. The excitation and fluorescence wavelengths are specific for each fluorophore, and the skilled person will know how to choose suitable wavelengths for both purposes.

In general, the correlation in step d includes the use of a pre-determined standard curve that expresses the relationship between the amount of contaminants and the amount of the detectable moiety under standard conditions (such as reaction time, temperature, etc).

The detection may be performed in a microtiter system (especially suited when the detectable moiety is determined via its interaction with another substance such as an antibody). In some embodiments, the liquid vehicle is passed directly from the effluent side of the filter to the microtiter plate, an effect that can be achieved by integrating the filter with the microtiter plate.

In some embodiments, the contaminants may be subjected to a signal-enhancing influence, either prior to step a or in step b, which may increase the overall sensitivity in a subsequent detection or favor subsequent detection of specific types of contaminants, or reduce detection of specific types of contaminants.

Such a signal-enhancing influence is typically selected from an enzyme-enhancing substance, a selective temperature or temperature range, a selective pH, a selective salt concentration, a non-selective growth-enhancer, and a selective growth-enhancing substance. The person skilled in the art is aware of the various possibilities available and will be able to select these in relation to the particular sample, contaminant of interest, substrate/enzyme combination and detection method.

In other embodiments, the signal may be enhanced by an incubation of the medium prior to step a. This incubation may include treatment with an enzyme inducing substance to enhance the detection of the detectable moiety (and thus a general enhancing effect because conversion of substrate is promoted), and/or subjecting the medium to a selective substance for yeast, fungi or bacteria (this has the effect of favoring detection of certain contaminants), and/or subjecting the medium to a non-selective growth-enhancer for microorganisms, and/or subjecting the medium to a substance capable of extracting cellular enzymes (comparable to the first alternative because it also promotes the conversion of substrate in step b).

In some embodiments, the above testing method may be used to determine if the water based wellbore fluid has no bacteria or if the water based wellbore fluid has large numbers of bacteria. In some embodiments, the testing method is sensitive enough to detect low, medium and high concentration of bacteria. In some embodiments, low concentrations may have a value of zero value, high concentrations may have values in the millions of colony-forming units (CFU), and medium concentrations may have values in between. In other embodiments, naturally occurring water chemistry, algae, mold, tannic acid, total suspended solids (TSS), and total dissolved solids (TDS) do not interfere with the above testing method. In still other embodiments, the above testing method is not interfered by oil field chemicals used in water treatment.

In some embodiments, the above method may be performed using a test kit. The kit may include at least one sterile filter device comprising a filter with a pore size sufficiently small to retain the contaminants on the filter's influent side, means for passing a known volume of medium through the filter (e.g. a syringe), an agent (e.g. a substrate as taught above) that upon interaction with the contaminants will release a detectable moiety, the amount of which can be correlated with the amount of contaminants that have interacted with the agent, and instructions that sets forth steps for a) obtaining a known volume of medium and passing it through the sterile filter device, b) contacting the influent side of the filter with the agent, c) allowing the agent to interact with contaminants that might be on the influent side of the filter, and d) quantitatively detecting the detectable moiety.

All the features characterizing this particular kit are described in U.S. Pat. No. 7,939,285, herein incorporated by reference in its entirety, meaning that the disclosures relating to sterile filter devices, agents that produce a detectable moiety may apply mutatis mutandis to embodiments of the kit and can be used as constituents therein, the instructions corresponding to the teachings herein relating to the exercise of embodiments of methods described, these teachings applying mutatis mutandis to the embodiments of the kit.

The above described test and test kit may be used on-site at oil or gas processing sites. In some embodiments, the sample may be a wellbore fluid and the sample may be taken prior to the wellbore fluid entering the wellbore or after the wellbore fluid has exited the wellbore. In yet other embodiments, the wellbore fluid may be a drilling fluid, a completions fluid, a fracturing fluid, or any fluid used in the production of oil and gas.

In some embodiments, a method may be provided which determines the concentration of a microbial population in a wellbore fluid; treats the wellbore fluid to reduce the microbial population and produce a treated wellbore fluid; and determines the concentration of the microbial population in the treated wellbore fluid. The treatment step and testing step may be repeated to produce a final wellbore fluid having an acceptable level of contaminants Although a few example embodiments have been described in detail above, those skilled in the art will readily appreciate that many modifications are possible in the example embodiments without materially departing from the use of rapid onsite bacteria test for oil and gas applications. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Further, it is the express intention of the applicant not to invoke 35 U.S.C. §112, paragraph 6 for any limitations of any of the claims herein, except for those in which the claim expressly uses the words 'means for' together with an associated function.

What is claimed is:

1. A method for treating oilfield water based solution comprising:
   a. determining a concentration of a microbial population in a wellbore fluid;
   b. after step a, treating the wellbore fluid to reduce the microbial population and produce a treated wellbore fluid; and
   c. after step b, determining a concentration of the microbial population in the treated wellbore fluid;
   wherein treating the fluid in :step b comprises subjecting the wellbore fluid to at least one treatment process selected from the group consisting of chemicals; UV; thermal; ionizing radiation; and non-ionizing radiation.

2. The method of claim 1, further comprising repeating treating the treated wellbore fluid to reduce the microbial population to produce a final wellbore fluid having an acceptable level of contaminants.

3. The method of claim 1, wherein determining the concentration comprises collecting at least one component of a wellbore fluid;
- exposing at least one contaminant in the at least one component to at least one substrate that will produce a detectable moiety; and
- performing a quantitative or qualitative detection of the detectable moiety.

4. The method of claim 1, wherein determining the concentration further comprises concentrating at least one contaminant in the at least one component to produce a concentrated sample.

5. The method of claim 1, wherein the method is performed onsite at an oilfied operation location.

* * * * *